United States Patent
Day et al.

(10) Patent No.: US 10,350,330 B2
(45) Date of Patent: Jul. 16, 2019

(54) METHOD TO PRODUCE INORGANIC NANOMATERIALS AND COMPOSITIONS THEREOF

(71) Applicant: The Curators of the University of Missouri, Columbia, MO (US)

(72) Inventors: Delbert E. Day, Columbia, MO (US); Ali Mohammadkah, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 191 days.

(21) Appl. No.: 15/510,201

(22) PCT Filed: Sep. 9, 2015

(86) PCT No.: PCT/US2015/049182
§ 371 (c)(1),
(2) Date: Mar. 9, 2017

(87) PCT Pub. No.: WO2016/040480
PCT Pub. Date: Mar. 17, 2016

(65) Prior Publication Data
US 2017/0247281 A1    Aug. 31, 2017

Related U.S. Application Data

(60) Provisional application No. 62/048,146, filed on Sep. 9, 2014, provisional application No. 62/048,148, filed on Sep. 9, 2014.

(51) Int. Cl.
C03B 37/005 (2006.01)
C03C 14/00 (2006.01)
(Continued)

(52) U.S. Cl.
CPC ............ *A61L 27/446* (2013.01); *A61K 47/02* (2013.01); *A61L 27/54* (2013.01); *A61L 27/58* (2013.01);
(Continued)

(58) Field of Classification Search
CPC .............................. C03B 32/00; C03B 32/02
See application file for complete search history.

(56) References Cited

U.S. PATENT DOCUMENTS 4,543,198 A  *  9/1985  Kamiyama ............ B82Y 30/00
                                                  252/62.56
5,250,355 A     10/1993  Newman et al.
(Continued)

FOREIGN PATENT DOCUMENTS

DE    10345625 A1    4/2005
FR    2946638 A1    12/2010

OTHER PUBLICATIONS

Brunner, T.J., Grass, R.N., and Stark, W.J., "Glass and bioglass nanopowders by flame synthesis", Chem. Commun., 2006, 1384-1386.*

(Continued)

*Primary Examiner* — Jason L Lazorcik
(74) *Attorney, Agent, or Firm* — Polsinelli PC (57) ABSTRACT

A solid state method of producing inorganic nanoparticles using glass is disclosed. The nanoparticles may not be formed until the glass is reacted with or degraded by contact with a fluid in vivo or in vitro.

13 Claims, 6 Drawing Sheets

(51) Int. Cl.

| | |
|---|---|
| C03C 3/064 | (2006.01) |
| C03C 3/15 | (2006.01) |
| C03C 4/00 | (2006.01) |
| A61L 27/44 | (2006.01) |
| C03B 5/193 | (2006.01) |
| C03B 32/00 | (2006.01) |
| A61K 47/02 | (2006.01) |
| A61L 27/54 | (2006.01) |
| A61L 27/58 | (2006.01) |
| C03C 3/19 | (2006.01) |

(52) U.S. Cl.
CPC .............. *C03B 5/193* (2013.01); *C03B 32/00* (2013.01); *C03B 37/005* (2013.01); *C03C 3/064* (2013.01); *C03C 3/15* (2013.01); *C03C 3/19* (2013.01); *C03C 4/0014* (2013.01); *C03C 14/004* (2013.01); *A61L 2430/32* (2013.01); *C03B 2201/62* (2013.01); *C03C 2204/00* (2013.01); *C03C 2214/04* (2013.01); *C03C 2214/30* (2013.01)

(56) References Cited

U.S. PATENT DOCUMENTS

| | | | |
|---|---|---|---|
| 6,358,531 B1* | 3/2002 | Day | A61K 9/1611 424/456 |
| 2005/0069592 A1 | 3/2005 | Fechner et al. | |
| 2006/0248982 A1 | 11/2006 | Yadav | |
| 2009/0069193 A1* | 3/2009 | Flemming | G01N 33/553 506/9 |
| 2010/0126218 A1 | 5/2010 | Shelestak et al. | |
| 2010/0233115 A1 | 9/2010 | Patel et al. | |
| 2010/0098768 A1 | 10/2010 | Andreescu et al. | |
| 2012/0126172 A1 | 5/2012 | Zhou et al. | |
| 2012/0281292 A1* | 11/2012 | Baca | C03C 17/007 359/601 |
| 2013/0116106 A1* | 5/2013 | Servin | B82Y 30/00 501/32 |
| 2013/0341511 A1 | 12/2013 | Shah et al. | |
| 2014/0030335 A1 | 1/2014 | Rzigalinski et al. | |
| 2014/0193499 A1 | 7/2014 | Da Fonte Ferreira et al. | |
| 2017/0247281 A1* | 8/2017 | Day | C03B 32/00 |

OTHER PUBLICATIONS

Salinas, A.J., Shruti, S., Malavasi, G., Menabue, L., Vallet-Regi, M., "Substituteion of cerium, gallium and zinc in ordered mesoporous bioactive glasses" Acta Biomaterialia, 7 (2011) 3452-3458.*

Ranasinghe, K.S., Singh, R., Day, D.E., Attenkofer, K., Staviski, E., Quinn, L.A., Patterson, D., Duenas, A., Evidence of the coesistence of multivalence cerium oxide nano-particles in a sodium borate glass, Journal of Non-Crystalline Solids 515 (2019)75-81.*

Allo, B.A. et al., Synthesis and Electrospinning of ε-Polycaprolactone-Bioactive Glass Hybrid Biomaterials via a Sol-Gel Process, Langmuir Article, 2010, vol. 26, No. 23, pp. 18340-18348.

International Search Report regarding PCT/US2015/049182 dated Dec. 14, 2015, 10 pages.

International Search Report regarding PCT/US2015/049184 dated Dec. 14, 2015, 8 pages.

Leonelli, C. et al., Synthesis and characterization of cerium-doped glasses and in vitro evaluation of bioactivity, Jounral of Non-Crystalline Solids, 2003, vol. 316, pp. 198-216.

Marquardt, L.M. et al., Effects of borate-based bioactive glass on neuron viability and neurite extension, Journal of Biomedical Materials Research A, 2014, vol. 102A, Issue 8, pp. 2767-2775.

Office Action dated Sep. 21, 2018 regarding U.S. Appl. No. 15/510,186, 15 pages.

Office Action dated Nov. 30, 2018 regarding U.S. Appl. No. 15/510,186, 15 pages.

Xie, Z. et al., Gentamicin-Loaded Borate Bioactive Glass Eradicates Osteomyelitis Due to *Escherichia coli* in a Rabbit Model, Antimicrobial Agents and Chemotherapy, 2013, vol. 57, No. 7, pp. 3293-3298.

Goh, YF et al., In-vitro characterization of antibacterial bioactive glass containing ceria, Ceramics International, 2014, vol. 40, pp. 729-737.

Yang, S. et al., Mesoporous bioactive glass doped-poly(3-hydroxybutyrate-co-3-hydroxyhexanoate) composite scaffolds with 3-dimensionally hierarchical pore networks for bone regeneration, Colloids and SufacesB: Biointertaces, 2014, vol. 116, pp. 72-80.

* cited by examiner

METHOD TO PRODUCE INORGANIC
NANOMATERIALS AND COMPOSITIONS
THEREOF

CROSS-REFERENCE TO RELATED
APPLICATIONS

This application claims the benefit of U.S. Provisional Patent Application No. 62/048,146 filed Sep. 9, 2014 and U.S. Provisional Patent Application No. 62/048,148 filed Sep. 9, 2014 the entire disclosures of which are both incorporated herein by reference.

FIELD OF THE INVENTION

The present invention relates to methods of forming nanoparticles within an inorganic glass and compositions thereof, and in particular to solid amorphous or semi-crystalline glass material that may form nanoparticles as the glass material degrades.

BACKGROUND

Nanotechnology is a relatively new era of science and technology that provides new possibilities for different applications. Scientists have found that the properties of materials at the nano scale (1-100 nm) level are different from those of the bulk material. Due to their small size and novel properties, new applications have been discovered in many industries such as automotive, medicine, chemistry, etc. Numerous research projects are underway to provide a fundamental understanding of nano scale phenomena, materials, and systems that have novel properties and functions.

Over the past 50 years, many methods have been developed to produce different types of inorganic nanomaterials with different sizes, shapes and properties. Most of these methods use a soluble salt (Nitrate, carbonate, etc.) to provide the desired ions in a solution and then use other chemicals or processes to precipitate or reduce (from an ion to neutral form (mostly for metals)) different forms of nanomaterials. However, nanomaterials can be formed through other routes like Sol-Gel processing, microemulsion, hydrothermal/solvothermal processing, templated synthesis, and biomimetic synthesis.

There is a need for new methods to create inorganic nanomaterials and nanoparticles that may then be used in a variety of applications such as tissue repair and regeneration, biomedical imaging, electronics, sensors, and coatings.

SUMMARY

Provided herein is a method for making nanoparticles including mixing a glass raw material with a nanoparticle base material to form a parent glass mixture; heating the parent glass material to a first temperature, forming a parent glass melt; cooling the parent glass melt to a second temperature to solidify the parent glass melt, forming a parent glass; and reacting or degrading the parent glass by contact with a solvent or fluid, wherein the nanoparticles are created as the parent glass reacts or degrades. The glass raw material may be a borate glass such as sodium tetraborate, or a borosilicate glass. The nanoparticle base material may be selected from a metal ion, a transition metal ion, an oxide, a carbonate, a rare earth oxide, a halide, a compound containing a cation, and combinations thereof. The nanoparticle base material may be selected from $CeO_2$, $Y_2O_3$, and $ZrO_2$. The nanoparticle base material may be a dopant. The dopant may be selected from Co, Ni, Cu, Ag, Au, Pt, Fe, Ru, Si, V, Cr, Mn, Fe, Ni, Zn, Sn, Sb, Zn, Ti, Y, Zr, W, La, Ce, Pr, Nd, Sm, Eu, Lu, Yb, Er, or combinations thereof. The parent glass may be selected from $Na_2O.2B_2O_3.xCeO_2$, $xNa_2O. 2xB_2O_3.(1-3x)Al_2O_3$, $xR_2O.yR'O.(1-x-y)B_2O_3$, and $xR_2O.yR'O.zR''_2O_3$. $m R'''_2O_5$. The parent glass may be $Na_2O.2B_2O_3.xCeO_2$ and x ranges from about 0.001 to about 0.30. The parent glass may be $xNa_2O. 2xB_2O_3.(1-3x)Al_2O_3$ and x ranges from about 0 to about 0.2. The parent glass may be $xR_2O.yR'O.(1-x-y)B_2O_3$; R is an alkali ion; R' is an alkaline earth ion; x ranges from about 0 to about 0.5; and y ranges from about 0 to about 0.5. The method of claim 10, wherein the alkali ion is Li, Na, or K and the alkaline earth ion is Mg, Ca, or Sr. The parent glass is $xR_2O.yR'O. zR''_2O_3$. $m R'''_2O_5$; R is an alkali ion; R' is an alkaline earth ion; R" is a modifier that form a R"2O3 oxide; R'" is a modifier that form a $R'''_2O_5$ oxide' such as phosphorus (P); x ranges from about 0 to about 0.5; y ranges from about 0 to about 0.5; z ranges from about 0 to about 0.2; and m ranges from about 0 to about 0,2. R may be Li, Na, or K, R' is Mg, Ca, or Sr, R" is Al or Fe, and R'" is P. The first temperature may range about 600° C. to about 1000° C. The second temperature ranges from about 20° C. to about 25° C. The parent glass may be reacted or degraded in vitro or in vivo. The method may further include a therapeutic agent. The method may further include bubbling the parent glass melt.

Further provided herein is a method for making nanoparticles including mixing a glass raw material with a nanoparticle base material to form a parent glass mixture; heating the parent glass material to a first temperature, forming a parent glass melt; cooling the parent glass melt to a second temperature to solidify the parent glass melt, forming a parent glass; treating the parent glass to form the nanoparticle base material into a plurality of nanoparticles suspended within the glass raw material; and contacting the glass raw material with a solvent or a fluid to release the plurality of nanoparticles. Treating the parent glass includes cooling and holding the melt at a third temperature for a period of time before cooling the melt to the second temperature. The third temperature may be between the first temperature and second temperature. The parent glass includes reheating the parent glass to a third temperature for a period of time and cooling the reheated parent glass to the second temperature. The third temperature may be between the first temperature and second temperature. The glass raw material may be a borate glass such as sodium tetraborate, or a borosilicate glass. The nanoparticle base material is selected from a metal ion, a transition metal ion, an oxide, a rare earth oxide, a carbonate, a halide, a compound containing a cation, and combinations thereof. The nanoparticle base material may be selected from $CeO_2$, $Y_2O_3$, and $ZrO_2$. The nanoparticle base material may be a dopant. The dopant may be selected from Co, Ni, Cu, Ag, Au, Pt, Fe, Ru, Si, V, Cr, Mn, Fe, Ni, Zn, Sn, Sb, Zn, Ti, Y, Zr, W, La, Ce, Pr, Nd, Sm, Eu, Lu, Yb, Er, or combinations thereof. The parent glass may be selected from $Na_2O.2B_2O_3.xCeO_2$, $xNa_2O. 2xB_2O_3.(1-3x)Al_2O_3$, $xR_2O.yR'O.(1-x-y)B_2O_3$, and $xR_2O.yR'O.zR''_2O_3$. $m R'''_2O_5$. The parent glass may be $Na_2O.2B_2O_3.xCeO_2$ and x ranges from about 0.001 to about 0.30. The parent glass may be $xNa_2O. 2xB_2O_3.(1-3x)Al_2O_3$ and x ranges from about 0 to about 0.2. The parent glass may be $xR_2O.yR'O.(1-x-y)B_2O_3$; R is an alkali ion; R' is an alkaline earth ion; x ranges from about 0 to about 0.5; and y ranges from about 0 to about 0.5. The alkali ion may be Li, Na, or K and the alkaline earth ion is Mg, Ca, or Sr. The parent glass may be $xR_2 O.yR'O. zR''_2O_3$. $m R'''_2O_5$; R is an alkali ion; R' is an alkaline earth ion; R" is a modifier that form a R"$_2$O$_3$ oxide; R''' is a modifier that form a R'''$_2$O$_5$ oxide, such as phosphorus (P); x ranges from about 0 to about 0.5; y ranges from about 0 to about 0.5; z ranges from about 0 to about 0.2; and m ranges from about 0 to about 0.2. R may be Li, Na, or K, R' is Mg, Ca, or Sr, R" is Al or Fe, and R''' is P. The first temperature may range from about 600° C. to about 1000° C. The second temperature may range about 20° C. to about 25° C. The parent glass may be reacted or degraded in vitro or in vivo. The method may further include a therapeutic agent. The method may further include bubbling the parent glass melt. Additionally provided herein is a method of delivering nanoparticles including placing parent glass comprising a nanoparticle base material in contact with a fluid within a region of interest; and reacting or degrading the parent glass to form and release the nanoparticles to the region of interest.

Provided herein is a method of delivering nanoparticles, including placing a parent glass comprising a plurality of nanoparticles suspended in a degradable glass within a region of interest; and reacting or degrading the parent glass by contacting the parent glass with a solvent or a fluid, to release the plurality of nanoparticles to the region of interest. Another aspect includes a nanoparticle-forming glass material, comprising a degradable glass doped with a nanoparticle base material, wherein the nanoparticle-forming glass material is capable of forming and releasing a plurality of nanoparticles when placed in contact with a solvent or a fluid., i.e., wherein reacting or degrading the nanoparticle-forming glass material in a solvent or a fluid forms and releases a plurality of nanoparticles into the solvent or fluid.

Further provided herein is a reactive glass material comprising a degradable glass and a plurality of nanoparticles suspended within the degradable glass, in contact with a solvent or fluid which reacts with the reactive glass material so that the reactive glass material releases the plurality of nanoparticles into the solvent or fluid. The contact with the solvent or fluid may be made in vitro or in vivo. An aspect includes a plurality of nanoparticles formed by the method including mixing a glass raw material with a nanoparticle base material to form a parent glass mixture; heating the parent glass material to a first temperature, forming a parent glass melt; cooling the parent glass melt to a second temperature to solidify the parent glass melt, forming a parent glass; and reacting or degrading the parent glass as described herein, wherein the nanoparticles are created as the parent glass reacts or degrades. Another aspect includes a plurality of nanoparticles formed by the method including mixing a glass raw material with a nanoparticle base material to form a parent glass mixture; heating the parent glass material to a first temperature, forming a parent glass melt; cooling the parent glass melt to a second temperature to solidify the parent glass melt, forming a parent glass; and treating the parent glass to form the nanoparticle base material into a plurality of nanoparticles suspended within the glass raw material; reacting or degrading the glass raw material to release the plurality of nanoparticles.

BRIEF DESCRIPTION OF THE DRAWINGS

The following figures illustrate various aspects of the disclosure.

FIGS. 2A-2B are TEM images of nanoparticles formed from the borate glass with the molar composition Na$_2$O.2B$_2$O$_3$.0.01CeO$_2$ reacted in DI-water at room temperature.

FIGS. 3A-3B are TEM images of nanoparticles formed from the borate glass with the molar composition Na$_2$O.2B$_2$O$_3$.0.01CeO$_2$ reacted in SBF at 37° C.

Corresponding reference characters and labels indicate corresponding elements among the views of the drawings. The headings used in the figures should not be interpreted to limit the scope of the claims.

DETAILED DESCRIPTION

Provided herein are methods of forming nanomaterials of different chemical compositions, sizes, and shapes within biodegradable, biocompatible inorganic glass.

As used herein, the term "subject" refers to an animal, including but not limited to a mammal including a human and a non-human primate (for example, a monkey or great ape), a cow, a pig, a cat, a dog, a rat, a mouse, a horse, a goat, a rabbit, a sheep, a hamster, a guinea pig).

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The term "fluid" as used herein refers to a liquid that is a body fluid, or has an ionic composition having an ionic composition comparable to that of a body fluid. In non-limiting example, a fluid can be a buffered saline solution. A "body fluid" originates from inside the organism of a subject, including for example blood, interstitial fluid, cerebrospinal fluid, or lymph.

Generally, nomenclatures used in connection with, and techniques of, cell and tissue culture, molecular biology, immunology, microbiology, and chemistry described herein are well known and commonly used in the art. The methods and techniques of the present disclosure are generally performed according to conventional methods well known in the art and as described in various general and more specific references that are cited and discussed throughout the present specification unless otherwise indicated. Any chemical, enzymatic or staining reactions, or purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry described herein are also well known and commonly used in the art. Standard techniques are used for chemical syntheses, chemical analyses, pharmaceutical preparation, formulation, delivery, diagnosis and treatment of all subjects, human and animal.

Accordingly, provided herein is a method of forming nanomaterials of different chemical compositions, sizes, and shapes within biodegradable, biocompatible inorganic glass. In an aspect, the nanomaterial may be a nanoparticle. The size, shape, and chemical composition of a given type of nanoparticle may be controlled by doping the parent glass with the desired amount of a chosen oxide, halide or other type of compound that may contain a desired cation. The parent glass for making the nanoparticles may be formed by melting the doped glass under controlled conditions (melting atmosphere, temperature and time) and cooling the glass in a controlled manner. The parent glass may then be reacted or degraded, in vivo or in vitro, forming and releasing the nanoparticles in the process.

The method of forming nanoparticles may be inexpensive, versatile, and adaptable for producing nanoparticles of many different compositions, sizes, and shapes suitable for medical and other applications. These nano size particles may be used in many applications such as tissue repair and regeneration, treating diseases, biomedical imaging, electronic devices, chemical sensing, coatings of metals and ceramics, etc. In an aspect, the cerium oxide nanoparticles described herein may be used in CNS (Central Nervous System) treatment applications. Cerium and yttrium oxide nanoparticles may be utilized in the repair and regeneration of CNS tissues in one aspect.

The biodegradable, biocompatible inorganic glass described herein can function as a delivery system and components of the glass may produce a beneficial physiological effect in vivo (for example, angiogenesis) in addition to releasing nanoparticles. Also, the glass may be multifunctional by doping it with different elements that may be delivered along with the nanoparticles in situ. In an aspect, the glass may deliver elements, like copper, that may be angiogenic.

The method of making nanoparticles from a glass may be cheaper than present methods of making nanoparticles since the raw materials are inexpensive compared to the salts (raw materials) being used in co-precipitation or other wet chemical methods of making nanomaterials. In addition, the nanoparticles made in a glass may have an indefinite shelf life at temperatures below about 100° C. Also the release of nanomaterials from the glass may be controlled in this method, which is an important advantage over other methods of producing nanomaterials.

I. Method of Making Nanoparticles

A method for making nanoparticles is provided herein. The method for making nanoparticles may include mixing the glass raw materials with nanoparticle base materials to form a parent glass mixture, heating the parent glass material to a first temperature, forming a parent glass melt, cooling the parent glass melt to a second temperature to solidify the parent glass melt, forming a parent glass into a desired shape, and reacting or degrading the parent glass, wherein the nanoparticles are created as the parent glass reacts or degrades. In an aspect, a borate glass containing cerium may be used to produce ceria nanoparticles.

The method of making nanoparticles herein is a solid-state (glassy-state) method to produce nanomaterials using a degradable glass. In an aspect, the nanomaterials may be nanoparticles. In this method, nanoparticles may be produced in two different ways. In the first method, the desired nanoparticle base material (metal ions, transition metal ions, rare earth oxide, etc.) may be dissolved in a glass melt to form the parent glass. In an aspect, the parent glass may be doped with an oxide, halide, or other compound containing a desired cation. Then the parent glass may be reacted or degraded in a desired solution in a laboratory (in vitro) or inside a mammal (in vivo). As the glass reacts or degrades the desired ions may be released and form nanoparticles of a desired composition/size. The second method may be to dissolve the desired material in the molten glass and then form the nanomaterials inside the glass using techniques such as controlled heat treatments, radiation, etc. The glass may then be reacted or degraded in vitro or in vivo and release the nanoparticles. In this second method, the glass network may disintegrate and dissolve in the solution while the insoluble nanoparticles remain in the solution, at least temporarily.

The glass and desired compounds may be mixed as powdered raw materials. In an aspect, the glass raw material may be a borate glass such as sodium tetraborate, or a borosilicate glass. In another aspect, the nanoparticle base material may be a dopant. The size, shape, and chemical composition of a given type of nanoparticle may be controlled by doping the parent glass with the desired amount of a nanoparticle base material chosen from an oxide, halide (F, Cl, I) or other type of compound (sulfate, oxalate, nitrate, etc.) that contains a desired cation, (Ce, Y, Zr, Gd, etc.) and (a) melting the doped glass under controlled conditions (melting atmosphere, temperature and time), and (b) cooling the glass in a controlled manner. In an aspect, powdered sodium tetraborate and $CeO_2$ may be mixed together to form a parent glass mixture of sodium borate glass.

In one aspect, the parent glass may have the molar composition of $Na_2O.2B_2O_3.xCeO_2$, where x ranges from about 0.001 to about 0.06. In another aspect, the parent glass may have the molar composition $xNa_2O.2xB_2O_3.(1-3x)Al_2O_3$, where x ranges from about 0 to about 0.2. In an aspect, the parent glass may have the composition $xR_2O.yR'O.(1-x-y)B_2O_3$, where R may be alkali ions such as Li, Na, K, etc. and R' may be alkaline earth ions such as Mg, Ca, Sr, etc. and where x ranges from about 0 to about 0.5 and y ranges from about 0 to about 0.5. In yet another aspect, the parent glass may be $xR_2O.yR'O.zR''_2O_3.mR'''_2O_5.(1-x-y-z)B_2O_3$, where R may be alkali ions such as Li, Na, K, etc. and R' may be alkaline earth ions such as Mg, Ca, Sr, etc., R'' may be modifiers that form a $R''_2O_3$ oxide such as Al, Fe, etc., and R''' may be modifiers that form a R'''$_2$O$_5$ oxide such as phosphorus (P) and x and y range from about 0 to about 0.5, and z and m range from about 0 to about 0.2.

Non-limiting examples of nanoparticle base material dopants for producing nanomaterials include ions of Co, Ni, Cu, Ag, Au, Pt, Fe, Ru. Non-limiting examples of nanoparticle base material dopants for producing oxides nanoparticles may include Si, V, Cr, Mn, Fe, Ni, Zn, Sn, Sb, Zn, Ti, Y, Zr, W, La, Ce, Pr, Nd, Sm, Eu, Lu, Yb, and Er. Two or more of these dopant elements may be combined within the nanoparticles. In an aspect, Y or La doped CeO$_2$ nanoparticles may be produced (co-doped cerium oxide-yttrium nanoparticles).

The method of making nanoparticles may use a solid amorphous (glass) or semi-crystalline (glass-ceramic) parent glass material to make the nanoparticles. For example, by giving the glass a prescribed heat treatment such that the desired nanoparticles are formed within the solidified melt (glass matrix), a chosen amount of nanoparticles may be delivered, in a controlled amount, to a desired site within a subject in several ways.

Figure 7:
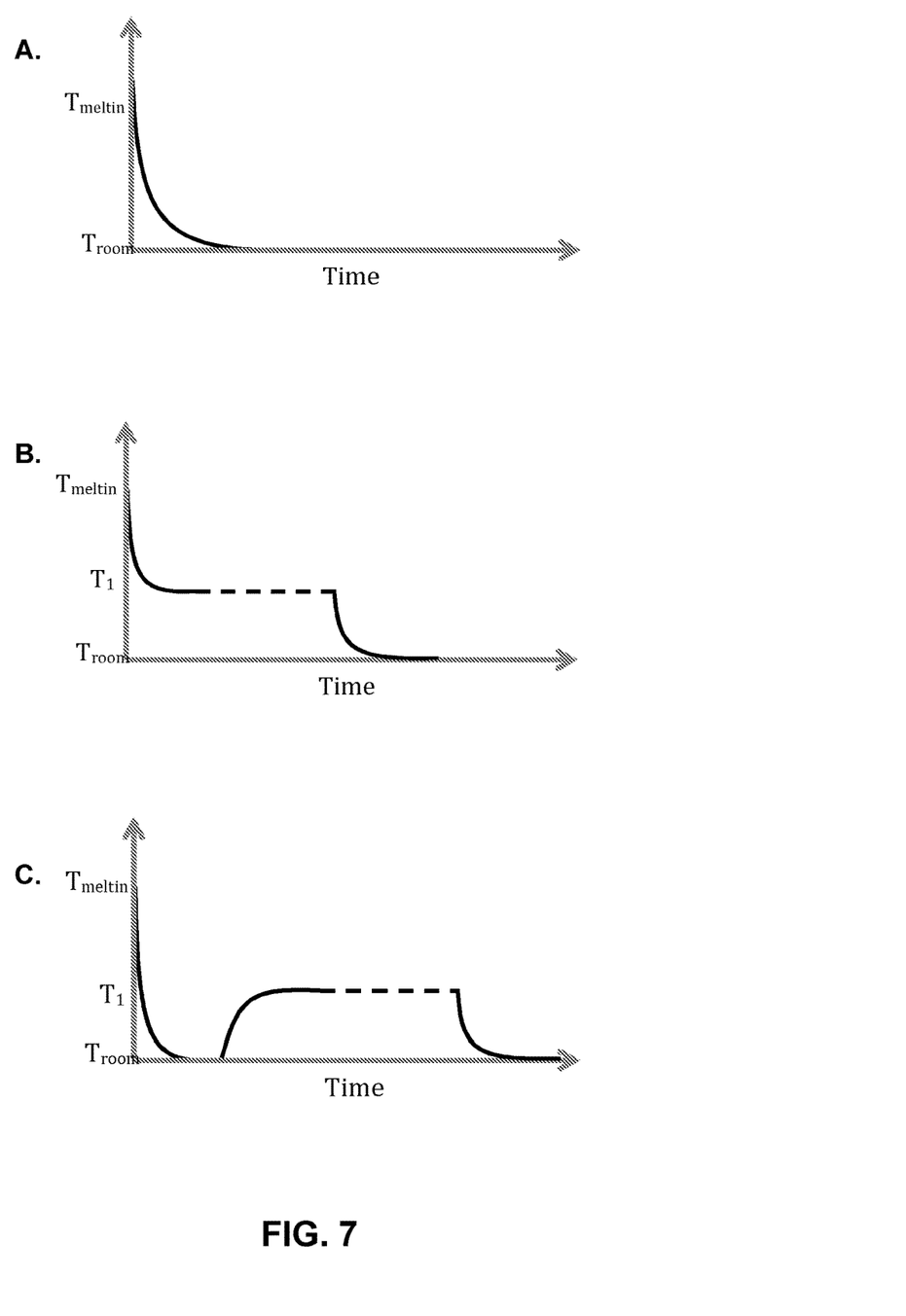
FIGS. 7A-C are graphs of various temperature/time profiles for heating and/or cooling the glass melt to form nanoparticles.

The parent glass mixture may be heated from about 600° C. to about 1000° C., forming a parent glass melt. In an aspect, the parent glass mixture may be heated to about 1000° C. for about 1 hour. The parent glass melt may be cooled to from about 20° C. to about 25° C. in various aspects. In an aspect, the parent glass melt may be cooled to room temperature to form the parent glass, as illustrated in FIG. 7A. In this aspect, the nanoparticles may form during the reaction or degradation of the glass upon contact with a solvent or a fluid.

In another aspect, cooling the melt may include cooling to a certain temperature ($T_1$), holding the melt/solid for a chosen time, and then cooling to room temperature, as illustrated in FIG. 7B. In this aspect, the nanoparticles may form during the holding at $T_1$ and may be released when the glass reacts or degrades in a chosen solution. In yet another aspect, cooling the melt may include cooling directly to room temperature ($T_{room}$) and after a certain time reheating the glass to a higher constant temperature ($T_1$) for a chosen time and then cooling the material to room temperature, as illustrated in FIG. 7C. In this aspect, the nanoparticles may form during the holding at $T_1$ and will be released from the glass as it reacts or degrades in a solvent or fluid. In various aspects, the melt may be cooled using any combination of the above methods.

In an aspect, the heat treatment may include bubbling the molten glass to form the nanoparticles within the parent glass. The gas composition may be reducing (forming gas, CO/CO$_2$ mixture), neutral (N$_2$, Ar, He), or oxidizing (pure oxygen). The gas flow rate may be from about 0.1 cm$^3$/min to about 1000 cm$^3$/min depending upon the size/volume of the melt. In various aspects, the gas flow rate may range from about 0.1 cm$^3$/min to about 1 cm$^3$/min, from about 0.5 cm$^3$/min to about 10 cm$^3$/min, from about 5 cm$^3$/min to about 50 cm$^3$/min, from about 25 cm$^3$/min, to about 75 cm$^3$/min, from about 50 cm$^3$/min to about 150 cm$^3$/min, from about 100 cm$^3$/min to about 300 cm$^3$/min, from about 200 cm$^3$/min, to about 400 cm$^3$/min, from about 500 cm$^3$/min, to about 700 cm$^3$/min, from about 600 cm$^3$/min to about 800 cm$^3$/min, from about 700 cm$^3$/min to about 900 cm$^3$/min, and from about 800 cm$^3$/min to about 1000 cm$^3$/min. The bubbling time may range from about 5 minutes to about 72 hours depending up on the melt composition and temperature, dopants in the melt, and melt size/volume. In various aspects, the bubbling time may range from about 5 minutes to about 1 hour, from about 30 minutes to about 2 hours, from about 1 hour to about 10 hours, from about 5 hours to about 24 hours, from about 15 hours to about 36 hours, from about 24 hours to about 48 hours, from about 36 hours to about 72 hours. The bubbling temperature may be any temperature where the viscosity of the melt is lower than about 10 poise.

The nanoparticles may be made and/or released in vitro by reacting or degrading the glass by contacting it with a desired liquid under certain reaction conditions (e.g., of temperature, pressure, pH, etc.). The solution may be a fluid as described herein, including for example a body fluid or simulated body fluid. Physiological conditions can be used. Alternatively the temperature for reacting the glass in vitro may range from about −20 to about 120° C. under ambient pressure or up to about 500° C. under higher pressures. The temperature for reacting or degrading the glass in vitro may range from about −20° C. to about 120° C. under ambient pressure or up to about 500° C. under higher pressures. In various aspects, the temperature may range from about −20° C. to about 10° C., from about 0° C. to about 50° C., from about 25° C. to about 75° C., from about 50° C. to about 100° C., from about 75° C. to about 120° C., from about 100° C. to about 300° C., from about 200° C. to about 400° C., and from about 300° C. to about 500° C. The pH of the solution for reacting or degrading the glass in vitro may range from about 2 to about 12. In various aspects, the pH of the solution may range from about 2 to about 6, from about 4 to about 8, from about 6 to about 10, and from about 8 to about 12. In one aspect, the glass composite materials can be designed to react or degrade over the span of minutes to years. Additionally, it will be understood that by changing various conditions such as temperature or solution compositions, it may be possible to form a variety of nanomaterials with special/different properties. In various aspects, the parent glass may react or degrade over about 5 minutes to about 1 hour, from about 30 minutes to about 2 hours, from about 1 hour to about 10 hours, from about 5 hours to about 24 hours, from about 15 hours to about 36 hours, from about 24 hours to about 48 hours, from about 36 hours to about 72 hours, from about 2 days to about 10 days, from about 5 days to about 20 days, from about 15 days to about 1 month, from about 1 month to about 6 months, from about 3 months to about 9 months, and from about 6 months to about 1 year.

In an aspect, the solvent or fluid may also contain organic or inorganic stabilizers or surfactants to stabilize the nanoparticles and prevent them from agglomerating. Non-limiting examples of stabilizers include tetrahydrofuran (THF), ethylene glycol (EG), hexadecylamine (HDA), mercaptosuccinic acid (MSA), poly(vinylpyrrolidone) (PVP), CTAB, and Polyvinyl Alcohol (PVA). By changing various parameters such as temperature or solution compositions, it is possible to form a variety of nanomaterials with special/different properties that is not possible to form inside a mammal. In one aspect, in vitro created nanoparticles may be used for other applications such as catalytic convertors or solid oxide fuel cells.

The nanoparticles may be made and/or released in vitro or in vivo. In one aspect, the biodegradable glass may be placed in contact with a fluid, for example at or near a region of interest in a subject, such that the nanoparticles are released into the body fluids at or near the region of interest as the glass degrades in the body fluids. In an aspect, the body fluids may be blood, interstitial fluids, cerebrospinal fluid, or lymph. A region of interest may be any soft, cartilaginous, or bone tissue that may benefit from nanoparticles released into an associated body fluid. For example, a region of interest may be a peripheral or central nerves or nerve cell, or may be the spinal column. A region of interest may comprise multiple distinct body tissues.

The parent glass may further include a therapeutic agent. This may include chemotherapeutics, growth factors, angiogenic compounds, or any other compound that may be beneficial to the region of interest. The therapeutic agent may diffuse out of the parent glass faster than the nanoparticles are formed. In an aspect, the therapeutic agent may provide a synergistic effect with the nanoparticles. The therapeutic agent may be for example copper, iron, zinc, or strontium.

II. Nanoparticles and Parent Glass

Provided herein are nanoparticles created through the reaction or degradation of a parent glass or a glass-ceramic material. The nanoparticles may have different compositions based on the doping of the parent glass. Non-limiting examples of nanoparticle compositions include, $CeO_2$, $Ce_2O_3$, $Y_2O_3$, and $ZrO_2$ and mixtures thereof.

In various aspects, the parent glass may include a borate glass such a sodium borate glass, or borosilicate glass. In one aspect, the parent glass may have the molar composition of $Na_2O.2B_2O_3.xCeO_2$, where x ranges from about 0.001 to about 0.30. In another aspect, the parent glass may have the molar composition $xNa_2O.2xB_2O_3.(1-3x)Al_2O_3$, where x ranges from about 0 to about 0.2. In an aspect, the parent glass may have the composition $xR_2O.yR'O.(1-x-y)B_2O_3$, where R may be alkali ions such as Li, Na, K, etc. and R' may be alkaline earth ions such as Mg, Ca, Sr, etc. and where x ranges from about 0 to about 0.5 and y ranges from about 0 to about 0.5. In yet another aspect, the parent glass may be $xR_2O.yR'O. zR''_2O_3. m R'''_2O_5.(1-x-y-z)B_2O_3$, where R may be alkali ions such as Li, Na, K, etc. and R' may be alkaline earth ions such as Mg, Ca, Sr, etc., R" may be modifiers that form a $R''_2O_3$ oxide such as Al, Fe, etc., and R''' may be modifiers that form a $R'''_2O_5$ oxide such as phosphorus (P) and x and y range from about 0 to about 0.5, and z and m range from about 0 to about 0.2.

Non-limiting examples of dopants for producing metallic nanomaterials include Co, Ni, Cu, Ag, Au, Pt, Fe, Ru, and their alloys. Non-limiting examples of dopants for producing oxides, phosphate, and borate compounds may include Si, V, Cr, Mn, Fe, Ni, Zn, Sn, Sb, Zn, Ti, Y, Zr, W, La, Ce, Pr, Nd, Sm, Eu, Lu, Yb, and Er. Two or more of these dopant elements may be combined within the nanoparticles. In an aspect, Y or La doped $CeO_2$ nanoparticles may be produced (co-doped cerium oxide-yttrium nanoparticles).

The parent glass may be semi-crystalline or non-crystalline/amorphous, and the nanoparticles may be crystalline or non-crystalline/amorphous. In an aspect, parent glass reacted or degraded in vivo or in vitro in SBF may generate non-crystalline/amorphous nanoparticles.

Using the methods described herein, very small nanoparticles may be produced, which may be much harder to produce through any other method currently available. For example, nanoparticles of $CeO_2$ with a size of 2 nm are not commercially available. In various aspects, the nanoparticles may be less than 10 nm. In an aspect, the nanoparticles created from the parent glass may range in size from about 2 nm to about 60 nm. The size of the nanoparticles may be affected by the composition of the parent glass, temperature, and pH of the solution.

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1

Preparation of Parent Glass and Nanoparticles

Figure 1:
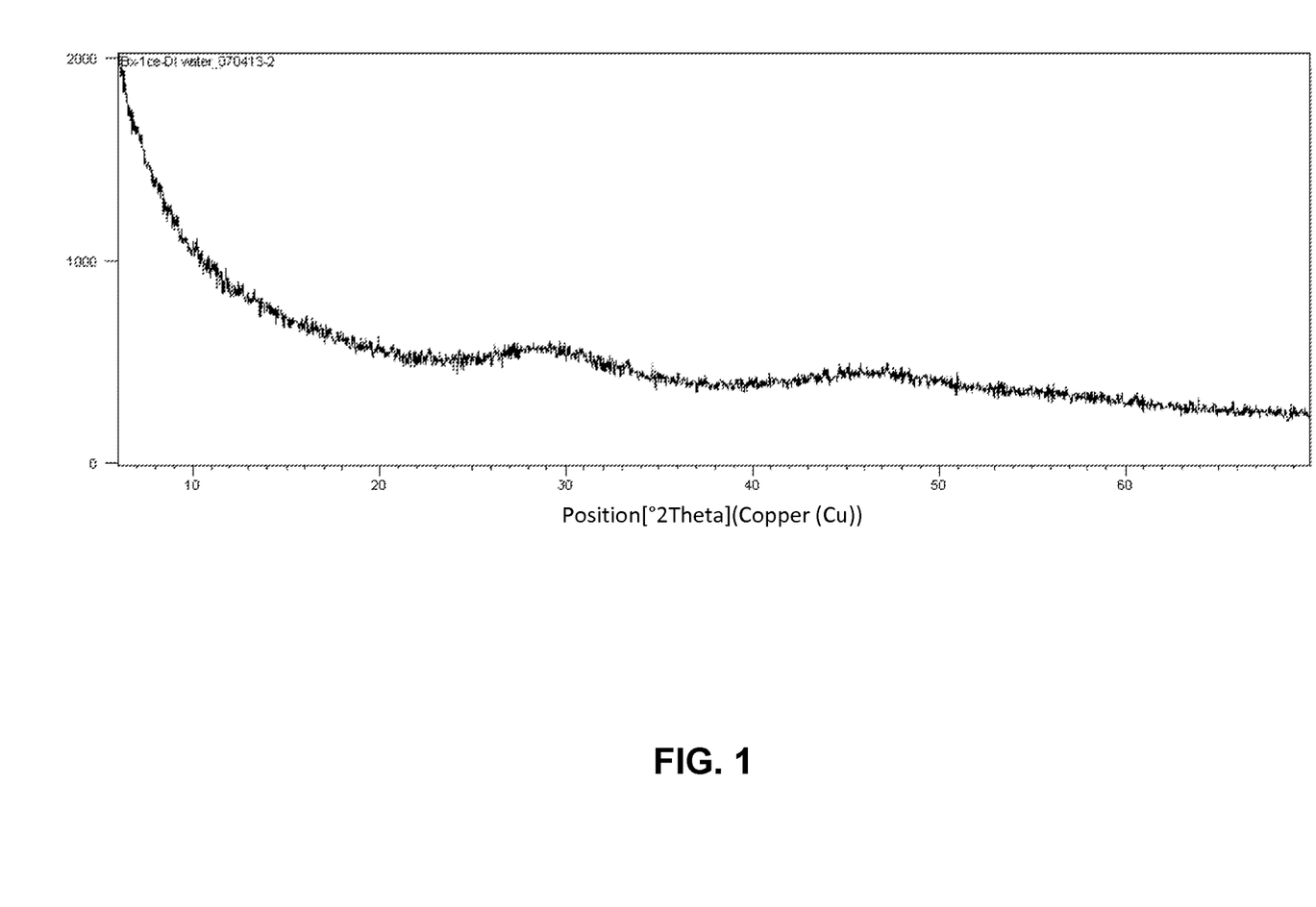
FIG. 1 is an x-ray diffraction pattern, showing the electron diffraction pattern for the as-made borate glass with the molar composition Na$_2$O.2B$_2$O$_3$.0.01CeO$_2$.

A sodium borate glass, with the molar composition of $Na_2O.2B_2O_3.xCeO_2$ (0.001<x<0.30), was prepared using sodium tetraborate (Alfa Aesar Ward Hill Mass., USA) and cerium oxide ($CeO_2$) (Alfa Aesar Ward Hill, Mass., USA). The powdered raw materials were mixed, the homogeneous mixture was melted in a platinum crucible at 1000° C. for 1 hour, and stirred several times. The melt was poured on a cold steel plate and cooled to room temperature forming a glass. FIG. 1 shows the XRD pattern of the as-made glass. The absence of diffraction peaks in the pattern in FIG. 1 indicates that no crystalline material (no identifiable nanoparticles) was present.

The glass was crushed to particles of less than 150 µm in diameter and 200 mg of the glass particles were reacted in 50 ml of DI water and simulated body fluid (SBF) at 37° C. for 12 hours. As the glass particles degrade the solution becomes cloudy due to formation of ceria nanoparticles. The solution was centrifuged to separate the nanoparticles from the solution, the residue was washed with fresh DI water, sonicated for 5 minutes, and then centrifuged for a second time. This procedure was repeated several times to insure that any boron or sodium that had dissolved from the glass was removed.

Figure 2A:
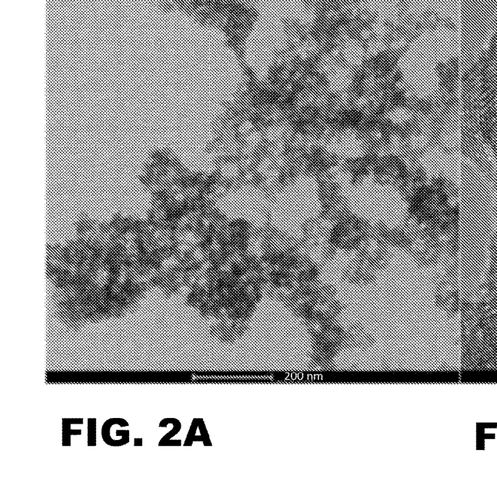
FIG. 2A is a low magnification TEM image of nanoparticle clusters. Scale marker is 200 nm.
Figure 2B:
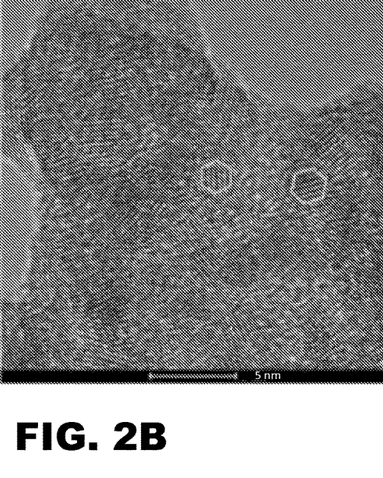
FIG. 2B is a higher magnification TEM image of nanoparticles (boundaries of two randomly selected individual nanoparticles identified with outline). Scale marker is 5 nm.

Finally, a drop of the solution containing the nanoparticles was placed on a 400 mesh copper TEM grid coated with a thin holey carbon, dried at 50° C., and then placed in the TEM. FIG. 2 shows TEM low and high magnification images of the $CeO_2$-x nanoparticles released from the borate glass as it reacted in DI water. The parallel patterns in the marked areas in FIG. 2 are lattice fringes (Planes of atoms in a certain crystal structure) of cerium oxide crystals. Each nanoparticle can be identified when the direction of these patterns changes because each nanoparticle/crystal has parallel planes (Boundaries of two individual nanoparticle identified by solid yellow lines). The cerium oxide nanoparticles were crystalline (as indicated by the lattice fringes) and had an average size of 2-3 nm.

Figure 3A:
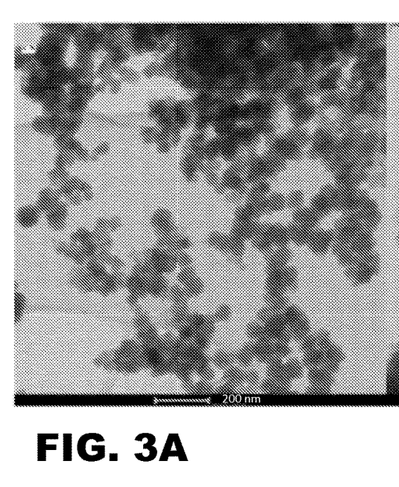
FIG. 3A is a low magnification TEM image of nanoparticle clusters. Scale marker is 200 nm
Figure 3B:
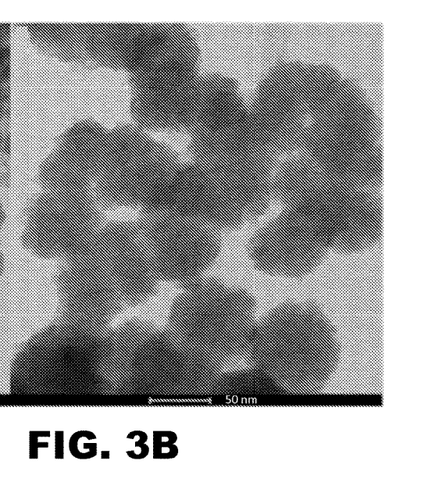
FIG. 3B is a higher magnification TEM image of nanoparticles. Scale marker is 5 nm.

FIG. 3 shows the nanoparticles formed in Simulated Body Fluid (SBF) solution. Simulated body fluid is a buffered solution with a pH of 7.4 and has a composition very close to human blood plasma. Table 1 shows the ion concentration of SBF and human blood plasma.

TABLE 1

| Ion | Concentration (mmol/dm³) | |
| --- | --- | --- |
| | Simulated body fluid (SBF) | Blood Plasma |
| $Na^+$ | 142.0 | 142 |
| $K^+$ | 5.0 | 5.0 |
| $Mg^{2+}$ | 1.5 | 1.5 |
| $Ca^{2+}$ | 2.5 | 2.5 |

TABLE 1-continued

| | Concentration (mmol/dm$^3$) | |
|---|---|---|
| Ion | Simulated body fluid (SBF) | Blood Plasma |
| Cl$^-$ | 148.8 | 103 |
| HCO$_3^-$ | 4.2 | 27 |
| HPO$_4^{2-}$ | 1.0 | 1 |
| SO$_4^{2-}$ | 0.5 | 0.5 |

Figure 4A:
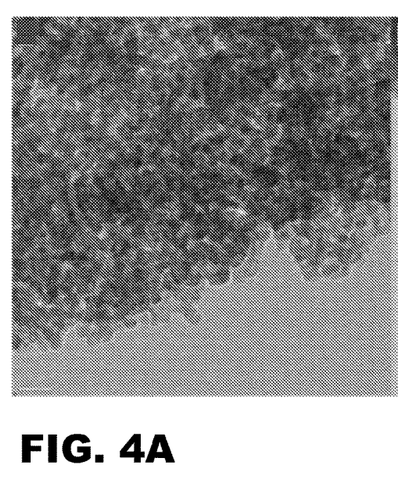
FIGS. 4A-4B are images of nanoparticles (agglomerated) formed with the borate glass with the molar composition of Na$_2$O.2B$_2$O$_3$.0.01CeO$_2$ doped with 1 wt. % Y$_2$O$_3$ (FIG. 4A) and 1 wt. % ZrO$_2$ (FIG. 4B) which was reacted in DI water at 37° C. The scale marker in the lower left hand corner is 20 nm.
Figure 4B:
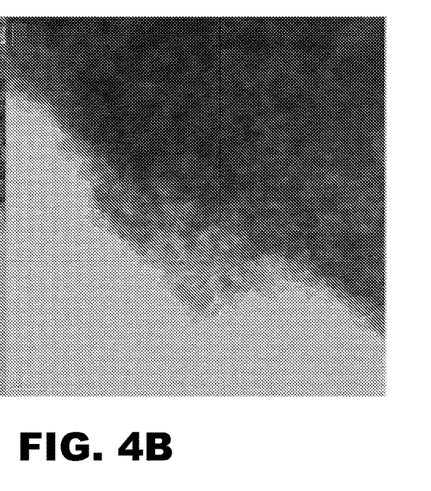

Nanoparticles formed in SBF were 50±10 nm in diameter and had an amorphous (non-crystalline) structure (no lattice fringes/parallel lines or patterns). Nanoparticles of yttrium and zirconium oxide may be formed in DI water using the same procedure (FIG. 4).

Example 2

Figure 5:
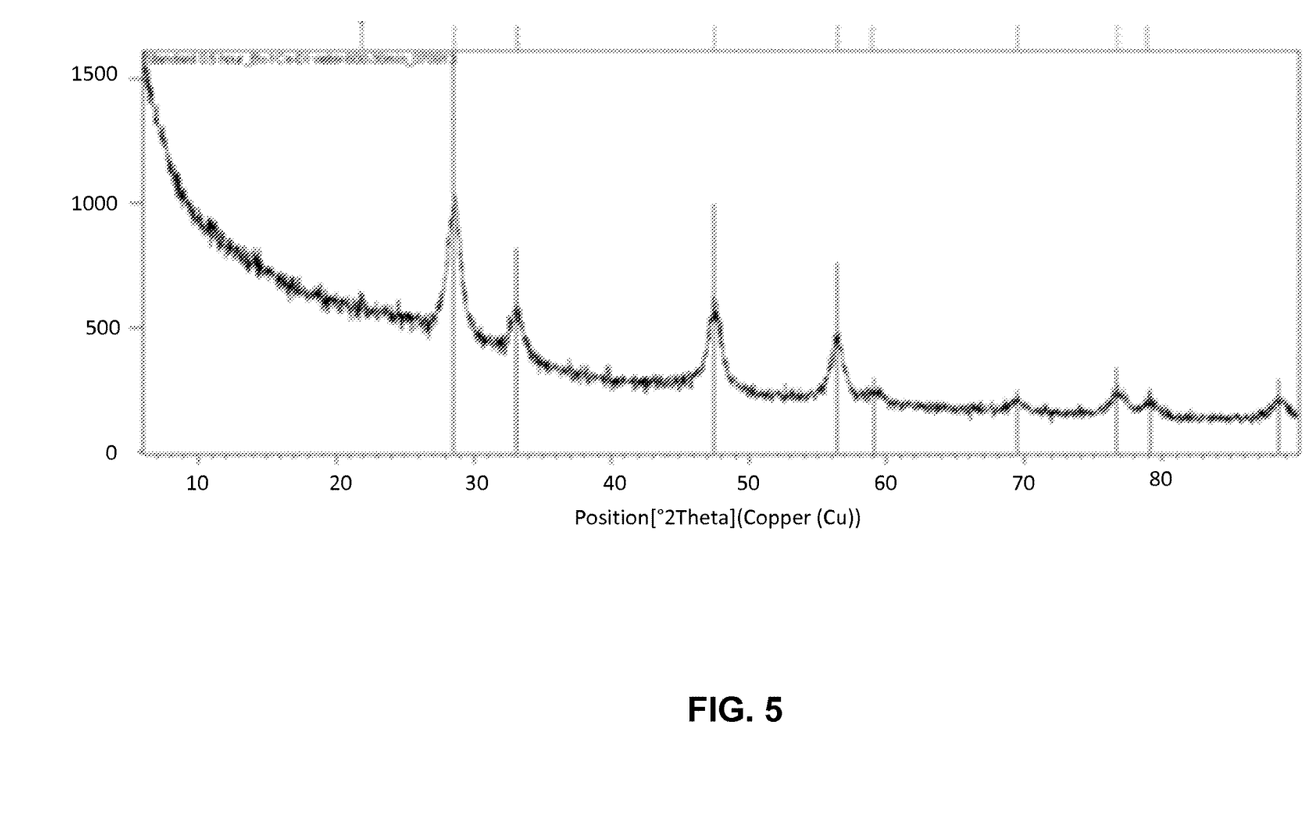
FIG. 5 is an x-ray diffraction pattern for the cerium oxide (CeO$_2$) nanoparticles after heating the precipitate of the reacted borate glass with the molar composition of Na$_2$O.2B$_2$O$_3$.0.01CeO$_2$ at 600° C. for 30 minutes containing cerium in DI water.

In another example, the cerium oxide residue (precipitate) that resulted from reacting the glass in DI water was dried and heated to 600° C. for 30 min (calcining). The XRD pattern for this calcined material is shown in FIG. 5 and the diffraction peaks show that it was crystalline CeO$_2$. The particle size was estimated to be about 6 nm using the Sherrer method from the broadening of the peaks in XRD pattern which is an indication of nano-crystalline crystals. The increase in size compared to the size obtained for TEM samples is due to the heat treatment and sintering, which occurred at 600° C.

Figure 6:
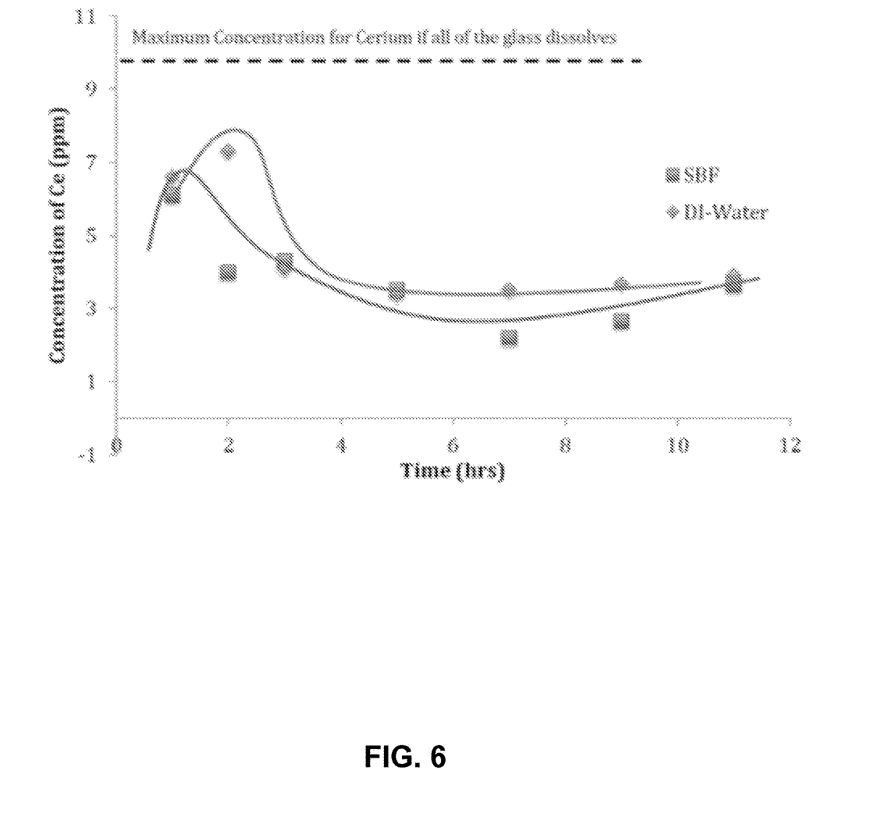
FIG. 6 is a release profile of Ce from Na$_2$O.2B$_2$O$_3$.0.01CeO$_2$ glass particles (<75 μm) that were reacted in DI water or in SBF at room temperature (about 25° C.).

The release of cerium oxide nanoparticles in DI water and SBF was determined using Inductive Coupled Plasma spectroscopy (ICP). Particles (<20 μm in diameter) of a borate glass with the molar composition of Na$_2$O.2B$_2$O$_3$.0.03CeO$_2$ were reacted in DI water and SBF at 22° C. and the concentration of cerium in the solution was measured. FIG. 6 shows the concentration of Ce in the DI water (A) and in SBF (B). The concentration of Ce initially rose due to degradation of the glass particles in the solution, but then declined due to the agglomeration of individual nanoparticles and the formation of larger clusters (>100 nm) and precipitates. The agglomerated nanoparticles were not detected by ICP.

Example 3

Table 2 provides examples of parent glass compositions, in mol % that were melted.

TABLE 2

| | #1 | #2 | #3 | #4 | #5 | #6 | #7 | #8 | #9 | #10 |
|---|---|---|---|---|---|---|---|---|---|---|
| B$_2$O$_3$ | 59 | 57 | 57 | 57 | 52 | 60 | 53 | 50.2 | 42 | 33 |
| Na$_2$O | 29 | 28 | 28 | 28 | 26 | 14 | 12 | 6.5 | 6 | 6 |
| CeO2 | 2 | 2 | 2 | 2 | 2 | 2 | 2 | 0.4 | 0 | 0 |
| Al2O3 | 10 | 7 | 4 | 0 | 0 | 0 | 0 | 0 | 0 | 0 |
| MgO | 0 | 6 | 5 | 7 | 15 | 8 | 15 | 8.3 | 8 | 8 |
| K$_2$O | 0 | 0 | 4 | 4 | 4 | 14 | 15 | 8.6 | 8 | 8 |
| Li2O | 0 | 0 | 0 | 2 | 2 | 2 | 0 | 0 | 0 | 0 |
| P2O5 | 0 | 0 | 0 | 0 | 0 | 0 | 3 | 1.9 | 2 | 2 |
| SiO2 | 0 | 0 | 0 | 0 | 0 | 0 | 0 | 0 | 10 | 19 |
| CaO | 0 | 0 | 0 | 0 | 0 | 0 | 0 | 24 | 24 | 23 |

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. A method for making nanoparticles, comprising:
   mixing a glass raw material with a nanoparticle base material to form a parent glass mixture; heating the parent glass mixture to a first temperature, forming a parent glass melt;
   cooling the parent glass melt to a second temperature to solidify the parent glass melt, forming a parent glass;
   heat or thermal treating the parent glass to form the nanoparticle base material into a plurality of nanoparticles suspended within the glass raw material, wherein contacting the glass raw material with the solvent or fluid releases the plurality of nanoparticles, and
   contacting the parent glass with a body fluid, wherein the parent glass is reacted or degraded in vivo.

2. The method of claim 1, wherein the glass raw material is sodium tetraborate.

3. The method of claim 1, wherein the nanoparticle base material is selected from a metal ion, a transition metal ion, an oxide, a rare earth oxide, a carbonate, a halide, a compound containing a cation, and combinations thereof.

4. The method of claim 1, wherein the parent glass is selected from Na$_2$O.2B$_2$O$_3$.xCeO$_2$, xNa$_2$O.2xB$_2$O$_3$.(1-3x)Al$_2$O$_3$, xR$_2$O.yR'O.(1-x-y)B$_2$O$_3$, and xR$_2$O.yR'O. zR"$_2$O$_3$.mR'"$_2$O$_5$, wherein
   R is an alkali ion;
   R' is an alkaline earth ion;
   R" is a modifier that forms a R"$_2$O$_3$ oxide;
   R'" is a modifier that forms a R'"$_2$O$_5$ oxide;
   x ranges from about 0 to about 0.5;
   y ranges from about 0 to about 0.5;
   z ranges from about 0 to about 0.2; and
   m ranges from about 0 to about 0.2.

5. The method of claim 4, wherein the alkali ion is Li, Na, or K, the alkaline earth ion is Mg, Ca, or Sr, R" is Al or Fe, and R'" is P.

6. The method of claim 1, wherein the first temperature ranges from about 600° C. to about 1000° C.

7. The method of claim 1, wherein the second temperature ranges from about 20° C. to about 25° C.

8. The method of claim 1, further comprising mixing a therapeutic agent with the glass raw material and the nanoparticle base material to form the parent glass mixture.

9. The method of claim 1, further comprising bubbling the parent glass melt.

10. The method of claim 1, further comprising:
    heat or thermal treating the parent glass to form the nanoparticle base material into a plurality of nanoparticles suspended within the glass raw material,
    wherein contacting the glass raw material with the solvent or fluid releases the plurality of nanoparticles.

11. The method of claim 1, wherein treating the parent glass comprises cooling and holding the melt at a third temperature for a period of time before cooling the melt to the second temperature or reheating the parent glass to a third temperature for a period of time and cooling the reheated parent glass to the second temperature.

12. The method of claim 11, wherein the third temperature ranges from the first temperature to the second temperature.

13. The method of claim 1, wherein the nanoparticles are created as the parent glass reacts with the fluid.

* * * * *